United States Patent
Terwee

(12) 
(10) Patent No.: US 7,981,154 B2
(45) Date of Patent: Jul. 19, 2011

(54) OPHTHALMIC SURGICAL METHOD

(75) Inventor: Thomas Terwee, Roden (NL)

(73) Assignee: AMO Groningen B.V., Santa Ana, CA (US)

( * ) Notice: Subject to any disclaimer, the term of this patent is extended or adjusted under 35 U.S.C. 154(b) by 1131 days.

(21) Appl. No.: 10/801,353

(22) Filed: Mar. 16, 2004

(65) Prior Publication Data

US 2004/0249454 A1 Dec. 9, 2004

Related U.S. Application Data

(60) Provisional application No. 60/455,762, filed on Mar. 19, 2003.

(30) Foreign Application Priority Data

Mar. 17, 2003 (SE) ........................................ 0300721

(51) Int. Cl.
*A61F 2/16* (2006.01)
(52) U.S. Cl. ....... 623/6.12; 623/6.16; 623/905; 424/427
(58) Field of Classification Search ................. 623/6.16, 623/905, 6.11, 6.56, 6.12; 424/427
See application file for complete search history.

(56) References Cited

U.S. PATENT DOCUMENTS

| | | | |
|---|---|---|---|
| 4,578,059 A | 3/1986 | Fabricant et al. | |
| 4,909,784 A * | 3/1990 | Dubroff | 604/521 |
| 5,576,345 A | 11/1996 | Månsson et al. | |
| 5,803,925 A * | 9/1998 | Yang et al. | 606/107 |
| 5,876,438 A * | 3/1999 | Kelleher et al. | 623/6.56 |
| 5,968,824 A * | 10/1999 | Spruce et al. | 435/375 |
| 6,200,799 B1 * | 3/2001 | Shaw et al. | 435/320.1 |
| 6,361,561 B1 * | 3/2002 | Huo et al. | 623/6.56 |
| 6,491,670 B1 | 12/2002 | Toth et al. | |
| 2002/0165522 A1 * | 11/2002 | Holmen | 604/521 |
| 2005/0191322 A1 * | 9/2005 | Norrby | 424/400 |

FOREIGN PATENT DOCUMENTS

| | | |
|---|---|---|
| EP | 0299467 | 1/1989 |
| WO | WO 02/15828 A2 * | 2/2002 |

OTHER PUBLICATIONS

Inan et al, Prevention of posterior capsule opacificatin by intraoperative single-dose pharmacologic agents, 2001, Elsevier Science Inc, Laboratory Science, J. Cataract Refract. Surg. vol. 27, Jul. 2001.*

* cited by examiner

*Primary Examiner* — Paul Prebilic
(74) *Attorney, Agent, or Firm* — AMO Groningen B.V.

(57) ABSTRACT

The present invention is in the field of ophthalmic surgery and relates to a method for the prevention of capsular opacification, especially after extraction of the natural lens from the lens capsule of the eye. Particular methods disclosed include replacing the natural lens with a capsule filling implant comprising an injectable material and injecting an agent capable of inhibiting the proliferation of lens epithelial cells, migration of lens epithelial cells, and/or production of extra-cellular matrix by lens epithelial cells into a space between the inserted capsule filling implant and the lens capsule using an instrument having a hydrophobic outer surface such that the composition reaches a germinative zone of the capsular bag.

42 Claims, 1 Drawing Sheet

OPHTHALMIC SURGICAL METHOD

RELATED APPLICATION

The present application claims priority under 35 U.S.C. §119 of U.S. Application Ser. No. 60/455,762 filed Mar. 19, 2003.

FIELD OF THE INVENTION

The present invention is in the field of ophthalmic surgery. In particular, it is directed to a method for the prevention of capsular opacification (CO), especially after extraction of the natural lens from the lens capsule of the eye.

BACKGROUND

The natural lens of the eye is contained within a capsular bag (in the present text, the terms "lens capsule", "capsule", "capsular bag" and "capsular sac" are used interchangeably), which is the basement membrane of lens epithelial cells held behind the iris and in front of the vitreous by the suspensory ligament called the zonules, and enveloping the natural lens. Capsular opacification (CO) is an opacification of the eye, which opacification is located on the inner surface of the capsular bag. It can be located posteriorly (posterior CO, PCO) and/or anteriorly (anterior CO, ACO). Capsular opacification can be caused by deposition or in-growth of cells, cell derivatives and/or fibers into the area that is transversed by the visual axis, and may also be caused by extra-cellular matrix that is produced by lens epithelial cells (in the following often referred to as LEC or LECs). The result is an occlusion of the optical axis of the eye and a concomitant clouding of vision. The cell deposits on the capsule (or on an implant that has replaced the lens) thus originate from the proliferation and migration of residual lens epithelial cells on the interior surface of the capsular bag, and from the production of extra-cellular matrix by these cells.

Capsular opacification often arises as a complication after surgical replacement of the natural lens of the eye with an implant. Such a replacement operation may be performed on patients suffering from cataracts, or in other circumstances. It is noted that lens removal with implantation replacement provides significant benefits to most cataract patients. Today, lens removal with implantation of artificial lenses is also increasingly carried out in non-cataractous eyes. An example is refractive lens exchange, which is often performed with the purpose of relieving presbyopia. Notwithstanding the usefulness of these operations, it is estimated that up to fifty percent of all patients who have had implants placed within the capsular bag will develop capsular opacification, also known as secondary cataract or after-cataract, within five years after surgery.

Extraction of the natural lens of the eye is among the most commonly performed operations in the world. In the following, a brief explanation of a common procedure will be given. In order to gain access to the natural lens, an incision is made in either the clear cornea, at the limbus, or in the sclera of the eye, whereby it becomes possible to introduce surgical instruments into the anterior segments of the eye. In the case of lens removal, an opening is made in the lens capsule, currently mainly using a capsulorhexis technique, in which a portion of the anterior membrane of the capsular bag is torn out to allow insertion of surgical instruments into the capsular bag for the purpose of extraction of the natural lens. The natural lens may be removed through application of any of a number of known techniques, including what is known as phacoemulsification.

Phacoemulsification is a method that involves application of ultra-sonic energy, or other forms of energy, to the natural lens with the purpose of breaking said lens into fragments. The fragments may then be aspirated from the capsular bag. The capsular bag remains substantially intact throughout this process of lens removal, with the exception of the portion removed to prepare access for the surgical instruments used in the extraction of the natural lens. After the removal of the natural lens (aphakia), an artificial intraocular lens (IOL) implant may be implanted within the capsular bag in order to mimic the transparency and the refractive function of a natural lens. Alternatively, a lens material is injected to fill the capsular bag and to create an artificial lens in situ. In addition, such lenses (AOL, accommodative intraocular lenses) may have the ability to restore the accommodative function of the natural lens, after the onset of presbyopia (loss of ability to accommodate).

Ophthalmic surgeons, aware of the problems associated with residual lens epithelial cells, typically take considerable care in trying to remove as many of the LECs as possible, prior to implantation of an artificial lens (IOL or AOL). However, despite these efforts, a significant number of LECs are usually left on the interior surface of the capsular bag, since the cells are difficult to see and often difficult to reach and virtually impossible to completely remove.

The most common treatment for post-operative PCO is the use of laser energy, which is applied to the posterior membrane of the capsular bag for the purpose of creating an opening in the posterior capsule (this is known as Nd-YAG capsulotomy). However, the laser energy applied to the posterior membrane of the capsular bag is ordinarily directed through the implant, and might damage the optic of said implant. Accordingly, it is preferred to prevent the occurrence of CO rather than treating CO at a later date through the application of laser energy. This is especially desirable when the implant is accommodating in response to ciliary muscle contraction, in which case a laser capsulotomy may compromise the accommodative ability of the lens.

Various procedures for the prevention of CO have been suggested in recent years. Many such procedures have included the introduction of chemicals into the capsular bag in order to destroy residual lens epithelial cells. However, few, if any, of these procedures have proven to be particularly successful in the prevention of CO, due to the fact that it is extremely difficult to destroy residual LECs without simultaneously destroying other cells within the eye, e g there exists a number of chemical agents that could kill the lens epithelial cells, however, said agents may also adversely affect other cells with in the eye, in particular corneal endothelial cells. Thus, selective destruction of residual LECs by exploitation of the cells' increased proliferative activity has been the primary approach for the prevention of CO.

Antimetabolites, such as 5-fluorouracil (5-FU) and daunomycin, have been injected into the capsular bags of eyes in attempts to prevent CO. However, for antimetabolite therapy to be effective, the agents must be present when the residual lens epithelial cell proliferation resumes at an indeterminate time following surgery. Sustained drug delivery systems have also been investigated as means for preventing CO. However, the effective time frame within when to apply these agents may likewise be difficult to determine. Thus, timing is difficult in the prevention of CO since it, as mentioned above, is believed to result primarily from the propagation of residual lens epithelial cells of the germinal layer and it is difficult to accurately predict when said cells might start to proliferate and migrate across the capsular bag into the optical zone.

Patent application WO 02/15828 (Bausch and Lomb) discloses methods for removing epithelial cells by injecting a composition comprising an agent after the natural lens has been removed from the capsular bag. The disadvantage with this technique is that the capsular bag is empty, i e the whole capsular bag is thus filled with the composition. Thus, much agent is needed, and in case of leakage there is a great risk that many cells outside the capsular bag, in particular corneal endothelial cells, may be damaged. Furthermore, the agent is not concentrated to the region of the inner wall of the capsular bag where the CO can be expected to be most severe. Another disadvantage is that the reaction time is limited to the length of time that the attending surgeon is able to wait until proceeding with the surgery, e g by implanting a lens or injecting a lens-forming composition. Conventionally, this will not be more than just a few minutes. Most of the toxic substances known need more than a few minutes to have, at least, some effect on the lens epithelial cells. Many of them need much more time.

Other workers have taken a slightly different approach to solving the problem of CO. Thus, U.S. Pat. No. 6,186,148 deals with the use of a substance affecting focal contacts mediating contacts between cells, and describes injection of said substance into the lens capsule prior to removal of the natural lens. U.S. Pat. No. 4,909,784 discloses a similar technique, wherein a cell-killing substance is injected between the capsule and the natural lens. This injection also takes place before lens removal. In these circumstances, when cells are treated prior to lens removal, there is only a limited time available for the agent to perform its activity, since in general surgery must be finished quite promptly, as described above. Also, in these circumstances, it is not possible to direct the agent exclusively to those cells that will be left in the capsule after lens removal. In contrast, the agent is unnecessarily also applied to cells that are subsequently removed physically upon removal of the lens.

Thus, there exists a need for a relatively simple, reliable and effective method of preventing capsular opacification in patients implanted with artificial lenses following lens extraction.

SUMMARY OF THE INVENTION

It is an object of the present invention to meet this need through the provision of an improved method for prevention of capsular opacification.

It is a related object of the present invention to provide such a method that allows long periods of lens epithelial cell treatment that do not affect and/or prolong the duration of surgical procedures of lens removal.

Another related object of the invention is to provide such a method that enables short surgery times coupled with a reliable removal of lens epithelial cell and/or inhibition of proliferation or migration thereof and/or production of extra-cellular matrix thereby.

Yet another object of the invention is to enable the inhibition of LECs through the action of an inhibitory agent, in which the amount used of such agent is minimized through positioning of said agent mainly where LECs proliferate.

These and other objects apparent to the skilled person from the disclosure herein are met by the invention as claimed in the independent claim.

Thus, a method for the prevention of capsular opacification is provided, which method comprises:
 a) creating an opening in a lens capsule of an eye;
 b) removing the natural lens from the lens capsule;
 c) inserting a capsule filling implant into the lens capsule; and
 d) injecting a composition into the space between the inserted implant and the lens capsule;
in which method the composition injected in step d) comprises at least one agent capable of inhibiting at least one of the following:
 proliferation of lens epithelial cells;
 migration of lens epithelial cells; and
 production of extra-cellular matrix by lens epithelial cells.

The basic insight forming the core of the present invention is that the objects of the invention may be achieved by performing the steps of the surgical procedure in the order given. Thus, the present invention enables emptying the capsule from the natural lens and any subsequent cleaning of the inside of the capsule in a standard manner, as well as the subsequent implantation of an IOL implant or the injection of a lens-forming composition. Only after this, the composition comprising at least one agent capable of alleviating CO by any of the actions referred to above is injected. Surgery may then be finished promptly, after which the composition will stay in place, performing e g its cell-inhibiting or cell-killing activity for as long as it is active. This can be from many minutes to days, depending on the choice of agent. The method of the present invention offers further benefits in that the surgical procedure of lens removal and replacement may be performed during a short time, meaning, in turn, that fewer patients will suffer from complications. There is also an economical benefit from the method of the invention, since the surgeon may perform more operations during a given period of time using the present method, compared to when using the more time-consuming methods previously known.

Furthermore, the method of the invention offers an additional improvement with respect to the known methods, in that the localization of the injected composition in the capsular bag is improved. This is due to the fact that the capsule filling implant will fill most of the empty space within the lens capsule, so that the composition will be able to perform its action in the space created between the capsule and the implant, where most, if not all, of the lens epithelial cells that remain after the extraction of the natural lens are located. In other words, a minimum amount of composition is needed for the achievement of maximum effect on LECs.

Additional advantages and aspects of the present invention are apparent to those of skill in the art to which it pertains, whether explicitly described or not, from the following detailed description, example and claims.

BRIEF DESCRIPTION OF THE DRAWINGS

FIG. 2A is a cross section of a lens capsule, the inside of which is treated with a composition through the introduction of a cannula into a rhexis. A, B: as in FIG. 1; 10: Pre-equatorial space; 11: Equatorial space; 12: Rhexis; 13: Cannula; X:

Injected composition. FIG. 2B is a side view of a capsule, illustrating 14: The circumferential edge of the capsule into the equatorial space.

DETAILED DESCRIPTION OF THE INVENTION

Figure 1:
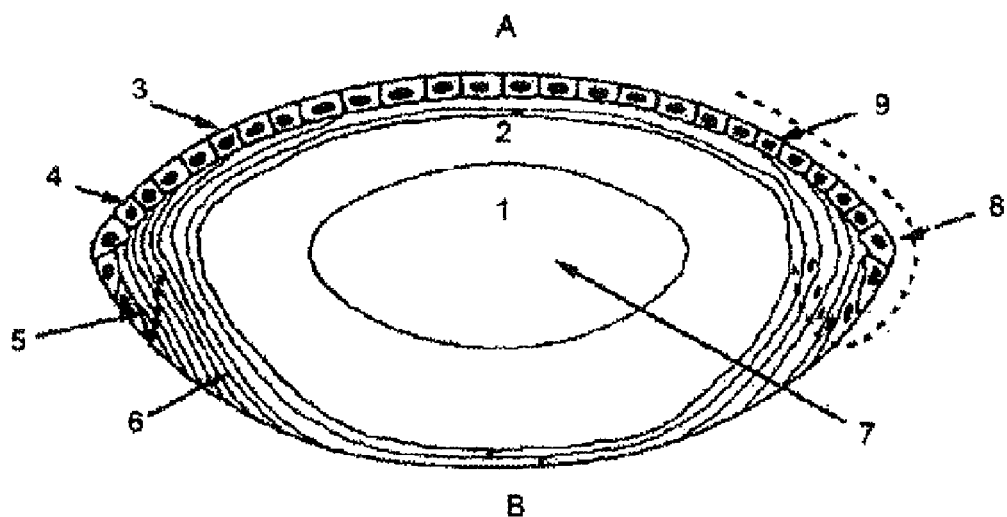
FIG. 1 is a schematic representation of the mammalian lens in cross section. Small arrowheads on the right in the figure indicate the direction of cell migration from the epithelium to the cortex. A: anterior pole; B: posterior pole; 1: Nucleus; 2: Cortex; 3: Surrounding capsule; 4: Epithelial cells; 5: Bow region; 6: Cortical fibers; 7: Nuclear fibers; 8: Equator; 9: Germinative zone. Adapted from Anderson R E, ed, Biochemistry of the Eye, San Francisco: American Academy of Ophthalmology 1983; 6:112.
Figure 2A:
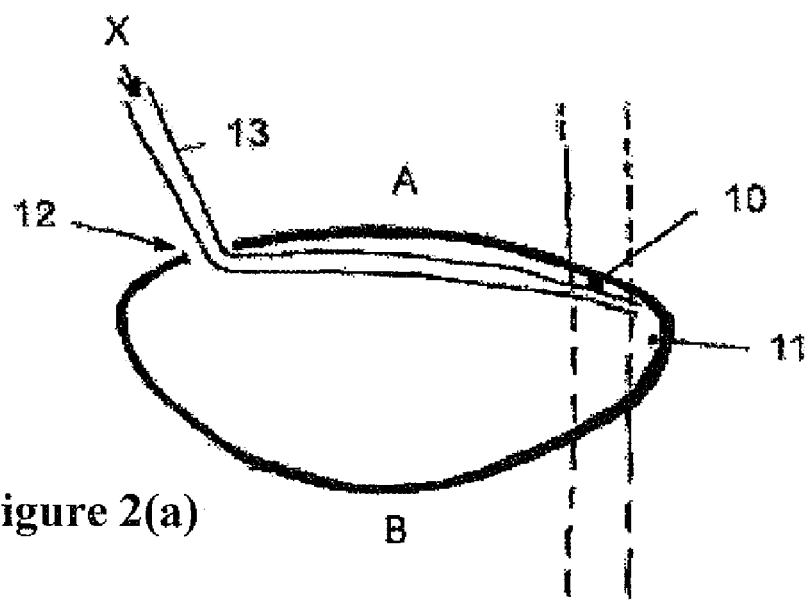
FIGS. 2A and FIG. 2B illustrate the method of the invention.
Figure 2B:
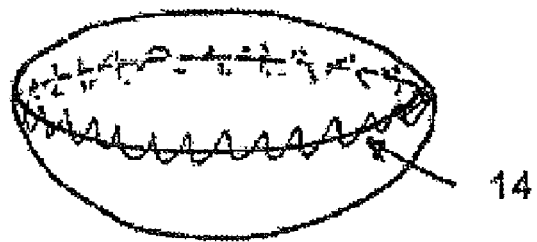

Reference numerals refer to the appended drawings and are supplied for illustration purposes only.

Step a) of the method according to the invention constitutes making an opening in a lens capsule of an eye. As explained in the Background section, this opening may suitably be made through first making an incision in the eye, and then creating a small rhexis (12) in the lens capsule. It is suitable in this regard that the opening created allows the entry into and removal from the lens capsule of for example surgical instruments and injection devices. However, the opening is suitably kept as small as possible. The size of the opening is mainly governed by what implant is to be inserted subsequently into the lens capsule in step c) of the method according to the invention. For some preferred implants envisioned in this regard, it is possible to keep the opening smaller than 3 mm, an opening size of 0.8-1.5 mm being more preferred. The size of the opening in this regard is for example the length of a linear incision or the diameter of an opening, created for example, but not limited to, using a punch, a scalpel, or other mechanical or physical means (e g laser) that are known to persons skilled in the field. The creation of such a small opening in the lens capsule lies within the skill of those practitioners that deal with such implants (e g injectable, curable lens compositions or hydrogel lenses; see below).

Removal of the natural lens from the lens capsule constitutes the next step b) of the method according to the invention, and may also be performed without undue burden by the person skilled in the art, for example as discussed in the Background section. Thus, the lens may suitably be separated from the capsular bag using any known hydrodissection technique (for example such as described and/or reviewed in any one of: Fine, J Cataract Refract Surg 18:508-512 (1992); Apple et al, Surv Ophthalmol 37(2):73-116 (1992); Faust, J Am Intraocul Implant Soc 10:75-77 (1984). Then, the natural lens may suitably be subjected to phacoemulsification for destruction thereof, and the resulting material removed by aspiration. As an example, the lens may be fragmented using an ultra-sonic probe or an impeller probe equipped with a high-speed impeller interfaced with irrigation and aspiration capabilities, as described in U.S. Pat. Nos. 5,437,678 and 5,690,641.

In step c) of the method according to the invention, a capsule filling implant is inserted into the capsular bag. Capsule filling implants suitably have the property of being closely aligned against the inside of the lens capsule, providing a minimum of space between implant and capsular wall. The capsule filling implant may be an artificial lens. Thus, such a lens is suitably a capsule filling lens, e g a lens that can be inserted into the lens capsule through a small rhexis. Examples comprise hydrogel lenses that gain their capsule filling form through taking up water upon implantation, preformed lenses that are rolled into a shape like a cigar and assume their capsule filling form under the influence of the body temperature, and lenses that are made from lens material injected into the lens capsule and then cured by heat or light. Materials suitable for injection in this regard are exemplified in e g PCT publications WO99/47185, WO00/22459, WO00/22460, WO01/77197 and WO01/76651. In other words, the implant suitably comprises an injectable material, which is capable of undergoing cross-linking to form a lens implant following injection thereof into the lens capsule.

Following the insertion of an implant into the lens capsule, a composition (X) is injected into the space between the inserted implant and the lens capsule. This constitutes step d) of the method according to the invention. This injection is preferably done using conventional equipment for ophthalmic surgery, such as for example using a cannula (13) of a suitable size. In a preferred method, the cannula, or other device for injection, is inserted between the inserted implant and the lens capsule and preceded as far as the circumferential edge of the capsule (14), whereupon injection of the composition is performed. In this way, the injection reaches the equatorial space (11) in the lens capsule, close to the germinative zones (9) of proliferating LECs.

Within the method of the present invention, step d) may be performed in different ways, using different amounts of the composition.

In a first alternative, the injection in step d) is performed in such a way that the composition injected is applied to the germinative zones (9) of epithelial cells, and in such a way that the central parts of the anterior (A) and posterior surfaces (B) of the lens capsule are kept essentially free from the composition. This has the advantage that an absolute minimum of the composition is used, while the most proliferatively active zones of LECs are reached and treated. Also, using this approach, a minimal amount of the composition will leak from the capsule during performance of the injection.

In another alternative, the injection in step d) is performed in such a way that the composition injected is applied to the whole of the inside of the lens capsule. This has the advantage that LECs in the whole of the interior of the capsule are reached.

In the case of a composition comprising one or more agents that are harmful to other parts of the eye tissue besides their effect on LECs, potential hazards arising from leaking of the composition from the lens capsule as a result of the injection in step d) may be controlled e g by removal of the composition by suction, by dilution of the composition to a concentration at which it does no harm, or by adding a neutralizing agent.

Regardless of how the injection in step d) is performed, it is furthermore essential that the choice of agent, and the choice of its mode of application, are such that the visual properties of the eye are not damaged or impaired to any significant extent. This means, in particular, that a composition injected in such a way that it is brought into contact with the whole of the interior of the capsule, including the anterior and posterior surfaces, must not damage the optical properties of those surfaces.

It may be preferred in step d) of the method according to the invention to use a particular instrument for the injection. In this regard, the provision of a hydrophobic outer surface on the injection instrument has been found advantageous. Thus, using an instrument with such a hydrophobic surface for the injection of agents, e g in aqueous solutions, may facilitate injection, in that less agent will follow the injection instrument back out of the lens capsule. The surface of the injection instrument may be rendered hydrophobic by equipping a standard steel cannula with a coating of a hydrophobic material, such as a silicone sleeve or a thin layer of a fatty substance. Alternatively, the injection instrument itself may be made of a hydrophobic material.

Some embodiments of the method according to the invention further comprise the step of sealing the opening in the lens capsule, for example to reduce the risks of inadvertent distribution of toxic agents to the tissues of the anterior chamber. Suitable means for such sealing are described in e g WO02/43632, WO02/43630 and WO00/49976. Sealing of the lens capsule may be performed through insertion of a sealing device in the opening before step d), which sealing device permits entrance into, and withdrawal from, the lens capsule of instruments for manipulation and/or injection. Such a sealing device can be introduced in the capsule at any time after step a) and prior to step d), since it does not form an obstacle to the manipulations within the lens capsule that need to be performed in accordance with the steps of the method of the invention. The primary advantage of introducing a sealing means before step d) is that it serves as a form of lid, thus keeping the amount of composition that may leak from the lens capsule to a minimum. This is especially desirable in the case when step d) is performed in such a way that the composition injected is applied to the whole of the inside of the lens capsule, since this entails using so much composition that the risk of leakage is apparent.

However, when the method according to the invention comprises a step of sealing the lens capsule, this sealing step may also be performed after the injection in step d).

The composition injected in step d) of the method of the present invention may have the effect of non-specifically or specifically destroying lens epithelial cells that remain on the interior surface of the capsular bag following removal of the natural lens. This is achieved by a composition that comprises at least one agent capable of inhibiting proliferation of, migration of and/or production of extra-cellular matrix by LECs. Such an agent may work in a plurality of ways to achieve the goal of preventing CO. This means that the agent may be one that lyses cell walls and/or disrupts cell attachment to the capsular bag. By destroying or damaging residual lens epithelial cells disposed on the interior surface of the capsular bag by whatever means, the cells are prevented from proliferating and/or migrating along or across the surface of the capsular bag and/or producing extra-cellular matrix, which will prevent the formation of capsular opacification.

The at least one agent comprised in the composition used in the method of the present invention is preferably present in a solution which is acceptable to the eye, more preferably in a physiologically isotonic solution. The physiologically isotonic solution may be a balanced salt solution, which comprises sodium chloride, potassium chloride, calcium chloride, magnesium chloride, sodium acetate and sodium citrate. Non-limiting examples of such solutions are Alcon BSS® or BSS Plus®, other known balanced salt solutions, Tyrode's solution, Hank's solution or Earle's solution. Furthermore, other sterile physiological isotonic solutions known to persons skilled in the art can be used in the method of the invention, as long as they are compatible with ocular tissue.

The at least one agent comprised in the composition injected in the method of the present invention is selected from cytotoxic agents, nucleic acid molecules that comprise a gene encoding a protein that induces the death of epithelial cells, basement membrane binding agents conjugated to cytotoxic agents, surfactants, hypertonic solutions, and chemical and enzymatic agents that release lens epithelial cells from the capsular bag membrane. Combinations of these agents are also included within the present invention.

Cytotoxic agents may be selected from the group consisting of saporin, ricin, methotrexate, 5-fluorouracil, daunomycin, doxorubicin, mitoxanthrone, vinca alkaloids, vinblastine, colchicine, cytochasins, monensin, mitomycin and ouabain. When LECs are contacted with any of these cytotoxic agents, the cytotoxic agent will be internalized, with the result that vital cellular processes of the LECs are inhibited.

Nucleic acid molecules may comprise a gene encoding a protein capable of inducing the death of lens epithelial cells, the gene being subject to transcriptional control specific to these cells. Said gene may be chosen from the group consisting of genes encoding a protein inducing cell death by necrosis and genes encoding toxic proteins. Said gene may preferably be a gene encoding a protein which induces apoptosis, or a gene involved in the process of apoptosis. Even more preferably, said gene encoding a protein capable of inducing the death of the LECs is chosen from the genes encoding p53, BAX, FLICE (also called caspase 8), TRAIL and TRAIL-R.

To enable the specific transcription of the nucleic acid molecule in lens epithelial cells, transcriptional control may be effected using the promoter of αA crystallin, the promoter of γD crystallin or the promoter of MIP (MP26). In particular, the promoter of αA crystallin or the promoter of γD crystallin is very specific to the lens epithelial cells.

The nucleic acid molecule is preferably provided in a vector. The vector can be for example a synthetic vector, which may transport the nucleic acid molecule as either DNA or RNA, or a viral vector. As viral vector, a vector can be used that is derived either from a virus of the family of retroviruses of the oncovirinae type (particularly the Moloney strain), advantageously used in a concentrated viral suspension, or from a virus of the lentiviridae type. The viral vector may also be derived from an adeno-associated virus (AAV) or from a virus of the family of the adenoviruses. The whole of a viral vector can be used, or just a fragment of the latter, as long as it will allow the gene encoding a protein capable of inducing cell death to penetrate into the lens epithelial cells that are to be destroyed. The vector used is preferably an episomal vector, which thus does not integrate itself in the genome of its target cells. Vectors suitable for use in the method of the present invention can for example be prepared as follows: A plasmidic construct of nucleic acid, preferably DNA, is realized, which contains a gene encoding a protein capable of inducing the death of LECs, the gene being subject to transcriptional control specific to said cells, in order to obtain the desired nucleic acid molecule, which is then isolated. Under preferred conditions of implementation of the process described above, a plasmidic construct of DNA is realized containing a gene encoding a protein inducing apoptosis (such as p53), subject to transcriptional control specific to the lens epithelial cells (for example using a promoter specific to said cells, in particular the promoter of αA crystallin or the promoter of γD crystallin), the gene encoding the protein inducing apoptosis preferably being followed by a polyadenylation sequence. The molecule of DNA described above can then be inserted in a vector, such as an adenoviral vector, to obtain the desired vector, which is then isolated.

Also suitable as agent for use in the composition to be injected are basement membrane binding agents conjugated to cytotoxic agents. The conjugated basement membrane binding agent bonds with basement membrane within the lens capsule and since the residual lens epithelial cells are disposed on the basement membranes within the lens capsule, the basement membrane binding agent will come into direct contact with the LECs when the binding agents are bonded to the basement membranes. The cytotoxic agent conjugated with the basement membrane binding agents is thereby brought into the presence of LECs, in order to enable destruction of any migrating or proliferating lens epithelial cells. In accordance with the present invention, at least one, but preferably only one for purposes of simplicity, suitable basement membrane binding agent is conjugated with at least one, but preferably only one for purposes of simplicity, cytotoxic agent. The at least one cytotoxic agent is preferably selected from the group consisting of ribosomal inhibitory proteins, antimitotic drugs and ionophores. The at least one basement membrane binding agent is preferably selected from the group consisting of poly-L-lysine, poly-D-lysine, fibronectin, laminin, type I, II, III and IV collagen, thrombospondin, vitronectin, polyarginine and platelet factor IV, conjugated to at least one cytotoxic agent. Most preferably, said cytotoxic agent is selected from ribosomal inhibitory proteins, while the at least one basement membrane binding agent most preferably is selected from poly-L-lysine and poly-D-lysine.

Ribosomal inhibitory proteins are preferred in the present invention, due to the fact that such proteins contain more inhibitory activity per microgram than other cytotoxic agents that can be used in connection with the method of the invention. However, other suitable cytotoxic agents are e g antimitotic drugs such as methotrexate, 5-fluorouracil, daunomycin, doxorubicin, mitoxanthrone, vinca alkaloids, vinblastine, colchicine, and cytochasins, and ionophores such as monensin and ouabain. A variety of known methods can be employed for conjugating the cytotoxic agent to the basement membrane binding agent.

The composition to be injected in step d) of the invention preferably comprises one of the agents disclosed above. However, the at least one agent is not limited to only those agents. Said agent may also be a surfactant, for example chosen from sodium dodecylsulfate (SDS) and polyoxyethylene sorbitan fatty acid esters (Tween); a hypotonic solution, for example pure water; or a hypertonic solution (i e a solution containing a large concentration of salt). Thus, since combinations of the agents listed in the present text also form part of the invention and may be comprised in the composition to be injected in step d), hypotonic or hypertonic solutions may be used either alone or in combination with any of the agents mentioned above. Surfactants and hypotonic or hypertonic solutions destroy lens epithelial cells by rupturing the cell membrane wall. Chemical and enzymatic agents that release lens epithelial cells from the capsular bag membrane are also suitable for use as agent in the present invention. Such agents include divalent cation chelators such as ethylene diamine tetraacetic acid (EDTA), trypsin, disintegrins, arginine-glycine-asparagine (RGID) peptide analogs, as well as antibodies directed against cell attachment receptors.

The inventive method will now be illustrated further through the recital of experiments conducted in accordance therewith. These examples are not intended to limit the scope of the invention as defined in the appended claims.

Example 1

After emptying the capsular bag of an explanted pig eye (fresh from the slaughter house) through a small (1.0-1.5 mm) capsulorhexis, the empty capsule was filled with a 2-component, polymerizable silicone polymer mixture. The rhexis was sealed with a silicone plug as described in WO02/43630.

A 22 mm long 27G cannula (Steriseal, Maersk Medical Ltd, type Rycroft) was brought into the capsule in such a way that the cannula protruded into the capsule through the rhexis, between the plug and the capsule, and then was introduced further between the polymerizing injected silicone polymer and the capsule until it reached the equatorial space.

A blue dye solution (containing trypan blue) was slowly injected into the equatorial space. The injected dye floated against the stainless steel cannula, straight back to the rhexis and outside the capsule into the anterior chamber, without noticeable spreading in the interface between the injected polymer and the capsular wall.

Example 2

After emptying the capsular bag of an explanted pig eye through a small (1.0-1.5 mm) capsulorhexis, the empty capsule was filled with a 2-component polymerizable silicone polymer mixture. The rhexis was sealed with a silicone plug as described in WO02/43630.

Over the 22 mm long stainless steel tube of a 27G cannula (Steriseal from Maersk Medical Ltd, type Rycroft), a 20 mm long silicone rubber tube (internal diameter 0.2 mm; external diameter 0.6 mm) was pushed, forming a tight silicone sleeve around the stainless steel cannula. By doing this, the outer surface of the cannula needle became hydrophobic. The sleeved cannula was brought into the capsule in such a way that the cannula protruded into the capsule through the rhexis, between the plug and the capsule, and then was introduced further between the polymerizing injected silicone polymer and the capsule, until it reached the equatorial space.

A blue dye solution (containing trypan blue) was slowly injected into the equatorial space. The injected dye filled the equatorial space completely around its circumference, and then rather evenly filled the interface area between the injected polymer and the capsular wall, both posteriorly and anteriorly. The injection of the dye could be stopped before the dye solution reached the rhexis. Accordingly, no dye entered into the anterior chamber of the pig eye.

The invention claimed is:

1. An ophthalmic surgical method, comprising:
   a) creating an opening in a lens capsule of an eye;
   b) removing the natural lens from the lens capsule;
   c) inserting a capsule filling implant comprising an injectable material into the lens capsule; and
   d) injecting a composition into a space between the inserted capsule filling implant and the lens capsule using an instrument having a hydrophobic outer surface such that the composition reaches a germinative zone of the capsular bag;
   in which method the composition injected in step d) comprises at least one agent capable of inhibiting at least one of the following:
   proliferation of lens epithelial cells;
   migration of lens epithelial cells; and
   production of extra-cellular matrix by lens epithelial cells.

2. Method according to claim 1, in which step d) is performed in such a way that the composition injected is selectively applied to the germinative zones of epithelial cells.

3. Method according to claim 1, in which step d) is performed in such a way that the composition injected is applied to the whole of the inside of the lens capsule.

4. Method according to claim 1, in which said instrument is a steel cannula with a hydrophobic coating.

5. Method according to claim 1, in which said instrument is made from a hydrophobic material.

6. Method according to claim 1, in which the size of the opening created in step a) is below 3 mm.

7. Method according to claim 6, in which the size of the opening created in step a) is from 0.8 to 1.5 mm.

8. Method according to claim 1, which further comprises sealing the opening in the lens capsule.

9. Method according to claim 8, in which said sealing is performed through insertion of a sealing device in the opening before step d), which sealing device permits entry into, and withdrawal from, the lens capsule of instruments for manipulation and/or injection.

10. Method according to claim 1, in which the capsule filling implant is an artificial lens.

11. Method according to claim 1, in which the injectable material is capable of undergoing cross-linking to form a lens implant following injection thereof into the lens capsule.

12. Method according to claim 1, in which the at least one agent is present in a physiologically acceptable solution.

13. Method according to claim 1, in which the at least one agent is present in a physiologically isotonic solution.

14. Method according to claim 1, in which the at least one agent is present in a hypotonic solution.

15. Method according to claim 1, in which the at least one agent is present in a hypertonic solution.

16. Method according to claim 1, in which the composition comprises a cytotoxic agent.

17. Method according to claim 16, in which the cytotoxic agent is selected from the group consisting of saporin, ricin, methotrexate, 5-fluorouracil, daunomycin, doxorubicin, mitoxanthrone, vinca alkaloids, vinblastine, colchicine, cytochasins, monensin, mitomycin and ouabain.

18. Method according to claim 1, in which the composition comprises a nucleic acid molecule comprising a gene encoding a protein capable of inducing the death of lens epithelial cells, the gene being subject to transcriptional control specific to said cells.

19. Method according to claim 18, in which the gene encoding a protein capable of inducing the death of lens epithelial cells is selected from the group consisting of genes encoding a protein which induces cell death by necrosis and genes encoding a protein which is toxic to lens epithelial cells.

20. Method according to claim 19, in which the gene encoding a protein capable of inducing the death of lens epithelial cells is a gene encoding a protein which induces apoptosis, or a gene involved in the process of apoptosis.

21. Method according to claim 18, in which said gene encoding a protein capable of inducing the death of lens epithelial cells is selected from the group consisting of genes encoding p53, BAX, FLICE, TRAIL and TRAIL-R.

22. Method according to claim 18, in which the gene encoding a protein capable of inducing the death of lens epithelial cells is provided within a vector.

23. Method according to claim 22, in which said vector is of the adenovirus type.

24. Method according to claim 1, in which the composition comprises at least one basement membrane binding agent, which is conjugated to at least one cytotoxic agent.

25. Method according to claim 24, in which the at least one cytotoxic agent is selected from the group consisting of ribosomal inhibitory proteins, antimitotic drugs and ionophores.

26. Method according to claim 25, in which the at least one cytotoxic agent is a ribosomal inhibitory protein.

27. Method according to claim 24, in which the at least one basement membrane binding agent is selected from the group consisting of poly-L-lysine, poly-D-lysine, fibronectin, laminin, type I collagen, type II collagen, type III collagen, type IV collagen, thrombospondin, vitronectin, polyarginine and platelet factor IV.

28. Method according to claim 27, in which the at least one basement membrane binding agent is poly-L-lysine or poly-D-lysine.

29. Method according to claim 1, in which the composition further comprises a surfactant.

30. Method according to claim 1, in which the composition further comprises a divalent cation chelator.

31. Method according to claim 1, in which the composition further comprises an arginine-glycine-asparagine (RGID) peptide analog.

32. Method according to claim 1, in which the composition further comprises an antibody directed against cell attachment receptors.

33. Method according to claim 19, in which said gene encoding a protein capable of inducing the death of lens epithelial cells is selected from the group consisting of genes encoding p53, BAX, FLICE, TRAIL and TRAIL-R.

34. Method according to claim 20, in which said gene encoding a protein capable of inducing the death of lens epithelial cells is selected from the group consisting of genes encoding p53, BAX, FLICE, TRAIL and TRAIL-R.

35. Method according to claim 19, in which the gene encoding a protein capable of inducing the death of lens epithelial cells is provided within a vector.

36. Method according to claim 20, in which the gene encoding a protein capable of inducing the death of lens epithelial cells is provided within a vector.

37. Method according to claim 25, in which the at least one basement membrane binding agent is selected from the group consisting of poly-L-lysine, poly-D-lysine, fibronectin, laminin, type I collagen, type II collagen, type III collagen, type IV collagen, thrombospondin, vitronectin, polyarginine and platelet factor IV.

38. Method according to claim 26, in which the at least one basement membrane binding agent is selected from the group consisting of poly-L-lysine, poly-D-lysine, fibronectin, laminin, type I collagen, type II collagen, type III collagen, type IV collagen, thrombospondin, vitronectin, polyarginine and platelet factor IV.

39. Method according to claim 1, further comprising keeping the composition in place for as long as the composition is active.

40. Method according to claim 2, in which step d) is performed in such a way that central parts of anterior and posterior surfaces inside the lens capsule are kept essentially free from the composition.

41. An ophthalmic surgical method, comprising:
   a) creating an opening in a lens capsule of an eye;
   b) removing the natural lens from the lens capsule;
   c) inserting a capsule filling implant into the lens capsule; and
   d) injecting a composition into the space between the inserted capsule filling implant and the lens capsule using an instrument having a hydrophobic outer surface such that the composition reaches a germinative zone of the capsular bag.

42. Method according to claim 41, further comprising keeping the composition in place for as long as the composition is active.

* * * * *